(12) United States Patent
Chu et al.

(10) Patent No.: US 8,670,948 B2
(45) Date of Patent: Mar. 11, 2014

(54) NUMERICAL APERTURE INTEGRATION FOR OPTICAL CRITICAL DIMENSION (OCD) METROLOGY

(71) Applicants: Hanyou Chu, Palo Alto, CA (US); Peilin Jiang, Santa Clara, CA (US)

(72) Inventors: Hanyou Chu, Palo Alto, CA (US); Peilin Jiang, Santa Clara, CA (US)

(73) Assignees: Tokyo Electron Limited, Tokyo (JP); KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/656,487

(22) Filed: Oct. 19, 2012

(65) Prior Publication Data

US 2013/0211760 A1    Aug. 15, 2013

Related U.S. Application Data

(63) Continuation of application No. 13/371,317, filed on Feb. 10, 2012.

(51) Int. Cl.
*G01N 37/00* (2006.01)
(52) U.S. Cl.
USPC .......................................................... 702/81
(58) Field of Classification Search
USPC .......................................................... 702/81
See application file for complete search history.

(56) References Cited

U.S. PATENT DOCUMENTS

| 7,388,677 B2 | 6/2008 | Vuong et al. |
| 2004/0004726 A1 | 1/2004 | Sezginer et al. |
| 2004/0184035 A1 | 9/2004 | Li et al. |
| 2007/0223011 A1 | 9/2007 | Jin et al. |
| 2010/0157315 A1 | 6/2010 | Bischoff |
| 2013/0158957 A1* | 6/2013 | Lee et al. ............ 703/1 |

OTHER PUBLICATIONS

Bischoff, Joerg et al., "Effective schema for the rigorous modeling of grating diffraction with focused beams", Applied Optics, vol. 50, No. 16, Jun. 1, 2011, 10 Pages.
International Search Report and Written Opinion for International Application No. PCT/US2012/070675 dated Apr. 10, 2013, 8 pages.

* cited by examiner

*Primary Examiner* — Aditya Bhat
(74) *Attorney, Agent, or Firm* — Blakely Sokoloff Taylor & Zafman LLP

(57) ABSTRACT

Provided are techniques for numerically integrating an intensity distribution function over a numerical aperture in a manner dependent on a determination of whether the numerical aperture spans a Rayleigh singularity. Where a singularity exists, Gaussian quadrature (cubature) is performed using a set of weights and points (nodes) that account for the effect of the Wood anomaly present within the aperture space. The numerical aperture may be divided into subregions separated by curves where the Wood anomaly condition is satisfied. Each subregion is then numerically integrated and a weighted sum of the subregion contributions is the estimate of the integral. Alternatively, generalized Gaussian quadrature (cubature) is performed where an analytical polynomial function which accounts for the effect of the Wood anomaly present within the aperture space is integrated. Points and nodes generated from a fit of the analytical polynomial function are then used for integration of the intensity distribution function.

21 Claims, 12 Drawing Sheets

NUMERICAL APERTURE INTEGRATION FOR OPTICAL CRITICAL DIMENSION (OCD) METROLOGY

CROSS-REFERENCE TO RELATED APPLICATIONS

This is a continuing application of application Ser. No. 13/371,317 filed Feb. 10, 2012, the disclosure of which is incorporated herein by reference in its entirety for all purposes.

TECHNICAL FIELD

Embodiments of the present invention are in the field of optical metrology, and, more particularly, relate to methods of integrating numerical aperture (NA) in optical critical dimension (OCD) metrology.

BACKGROUND

OCD metrology, also known as scatterometry, is a rapidly evolving technique for non-destructive dimension metrology utilized for in-line dimensional characterization of fabricated device structures. In the semiconductor industry for example, test grating structures may be fabricated along with the semiconductor device structures and these test grating structures may be optically characterized as a means of monitoring the fabrication processing.

Generally, OCD metrology entails simulating electromagnetic spectral information and comparing the simulated spectral information with measured spectral information collected from a sample grating illuminated on a workpiece (e.g., semiconductor wafer). As shown in FIG. 1, for an OCD metrology tool 100, the measured spectral information derived from the detector 110 is a result of the numerical aperture (NA) of the lens(es) 115 in the optical path which define a range of polar and azimuthal angles of incidence $(\theta, \phi)$ over which the optical system 116 operates. As shown in FIG. 1, the angular spectrum may be decomposed into rays about a chief ray (defined at $\theta = \theta_0$ and $\phi = 0$) which are then each modeled as a plane wave to produce a scattering function $S(\theta, \phi)$ through rigorous computation of a diffraction scattering matrix by a technique such as rigorous coupled wave analysis (RCWA).

Because RCWA calculations are computationally intensive, it is advantageous to average the optical signature over sampled incident directions. Generally, averaging of the optical signature entails integrating over an aperture (circular, rectangular, or otherwise). Such integration can be estimated by numerical quadrature using a technique such as Gaussian quadrature (1D) or cubature (2D) in which a weighted sum of a function is evaluated at n selected points (nodes) $x_i$ within the aperture space $\Sigma_{i=1}^{n} w_i f(x_i)$ as an approximation of $\int_a^b f(x)dx$, where each computation of $f(x_i)$ entails the intensive RCWA calculation.

For computing the nodes $x_i$ and weights $w_i$ of Gaussian quadrature (cubature) rules, the integrand function is preferably smooth. However, as a function of the illumination wavelength, numerical aperture, and dimensions of the grating, one or more Rayleigh singularities may occur within the numerical aperture space. Such a condition is also known as a Wood anomaly. Where Wood anomalies are not considered during numerical integration, convergence behavior for the numerical aperture average may be above measurement precision and/or be disadvantageously slow.

With smaller spot sizes often desirable for reducing the area of the workpiece 120 occupied by a target grating 125, a larger numerical aperture is desirable and Wood anomalies become more frequent. Techniques specially designed to integrate a numerical aperture spanning a Wood anomaly can therefore advantageously improve the simulated spectral information used in OCD measurement.

BRIEF DESCRIPTION OF THE DRAWINGS

Embodiments of the present invention are illustrated by way of example, and not limitation, in the figures of the accompanying drawings in which.

DETAILED DESCRIPTION

Figure 1:
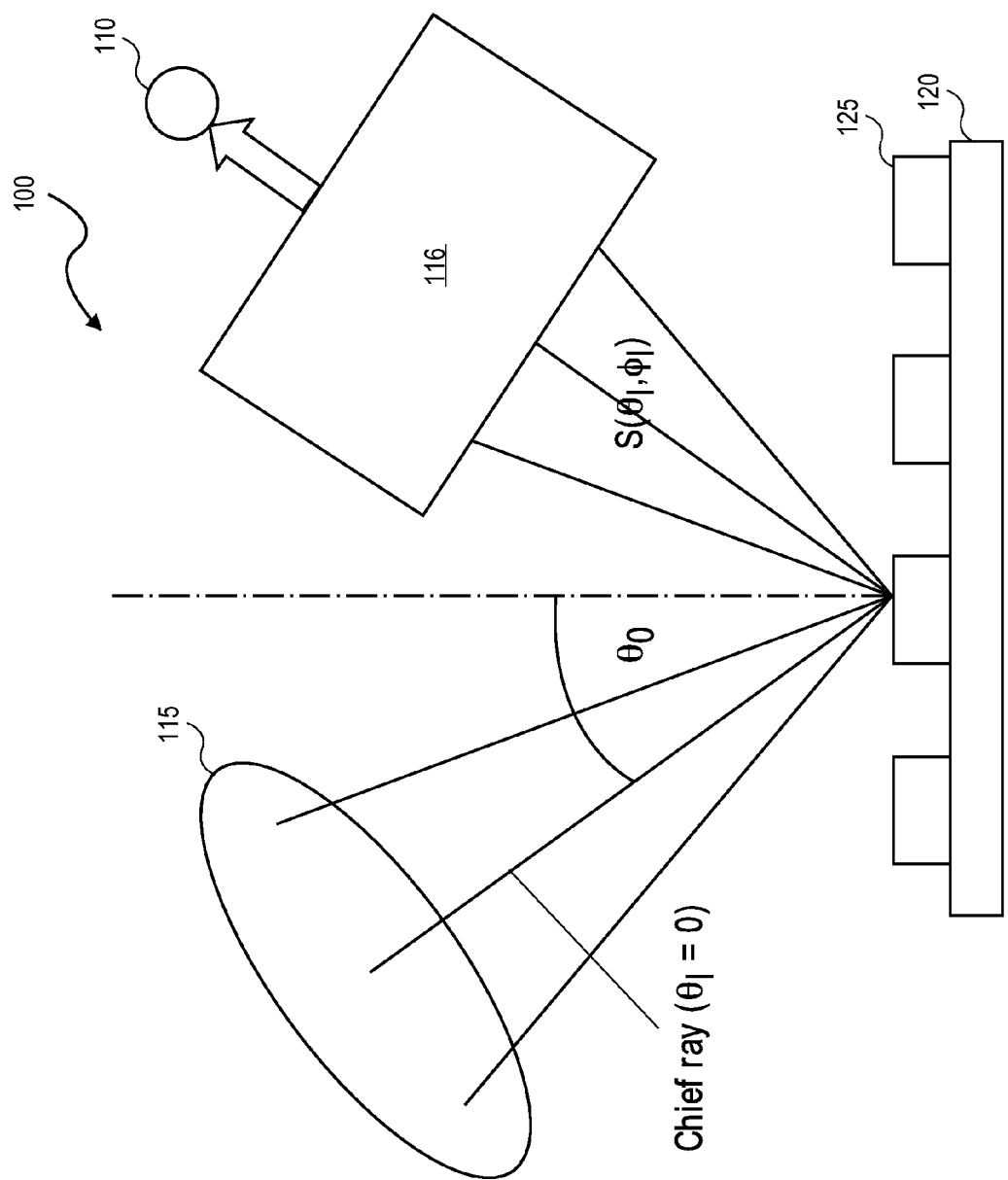
FIG. 1 illustrates a system for optical critical dimension (OCD) measurement, in accordance with an embodiment of the present invention.

In the following description, numerous details are set forth. It will be apparent, however, to one skilled in the art, that the present invention may be practiced without these specific details. For example, while the present methods are described in the context of scatterometry for diffraction grating parameter measurements, it should be appreciated that the methods may be readily adaptable to other contexts and applications by one of ordinary skill in the art.

In some instances, well-known methods and devices are shown in block diagram form, rather than in detail, to avoid obscuring the present invention. Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

Some portions of the detailed descriptions provide herein are presented in terms of algorithms and symbolic representations of operations on data bits within a computer memory. Unless specifically stated otherwise, as apparent from the following discussion, it is appreciated that throughout the description, discussions utilizing terms such as "calculating," "determining," "estimating," "storing," "collecting," "displaying," "receiving," "consolidating," "generating," "updating," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein include automated techniques for numerically estimating numerical aperture integrals. Generally, the techniques may be conceptualized as being dependent on a determination of whether the numerical aperture spans a Rayleigh singularity, as illustrated in the flow diagram for method 200 in FIG. 2. Parameters defining the incident light wavelength (λ), numerical aperture space size (value), and shape (e.g., circular, rectangular) are received at operation 205, as are polar and azimuth angles of incidence (θ), (φ). Such parameters are generally known for a given optical metrology system and may be entered by an operator of the system as a configuration parameter, etc. For example, incident angle θ is typically either normal or will be 60°-70° and numerical aperture values may range from low (e.g, <0.1) to high (e.g., between 0.9 and 0.95).

Figure 4A:
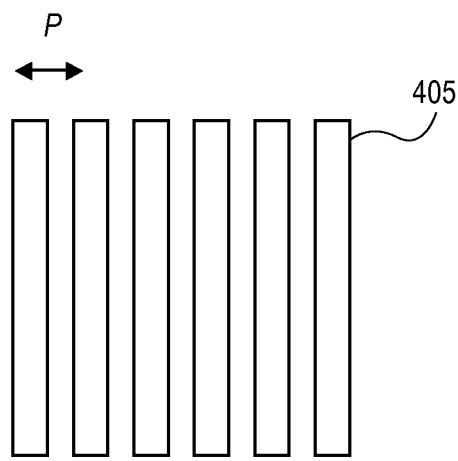
FIG. 4A is a plan view schematic of a 1D periodic structure for which electromagnetic spectral information is determined for an optical system having a numerical aperture integrated using the methods in FIG. 3A or FIG. 3B, in accordance with embodiments of the present invention.
Figure 4B:
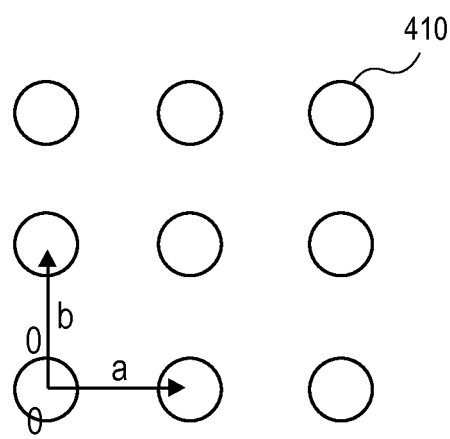
FIG. 4B is a plan view schematic of a 2D periodic structure for which electromagnetic spectral information is determined for an optical system having a numerical aperture integrated using the methods in FIG. 3A or FIG. 3B, in accordance with embodiments of the present invention.

Similarly, characteristics of the target diffracting structure are also received at operation 205. For example, diffracting structure pattern parameters are entered establishing whether the test structure is a 1D line-space grating, 2D orthogonal array, or 2D crossed structure array. FIG. 4A is a plan view schematic of a 1D periodic structure 405 for which electromagnetic spectral information may be determined for an optical system having a numerical aperture integrated using the methods described herein. For the 1D structure 405, a number of periods and/or pitch P may be predetermined as a configuration parameter for the methods described herein. FIG. 4B is a plan view schematic of a 2D periodic structure 410 for which electromagnetic spectral information may be determined for an optical system having a numerical aperture integrated using the methods described herein. For the 2D structure 410, a and b are grating periods in orthogonal directions (e.g., x and y). Although the illustrated 2D structure 410 is orthogonal, a crossed 2D structure where a and b are not equal, may also be utilized.

Figure 2:
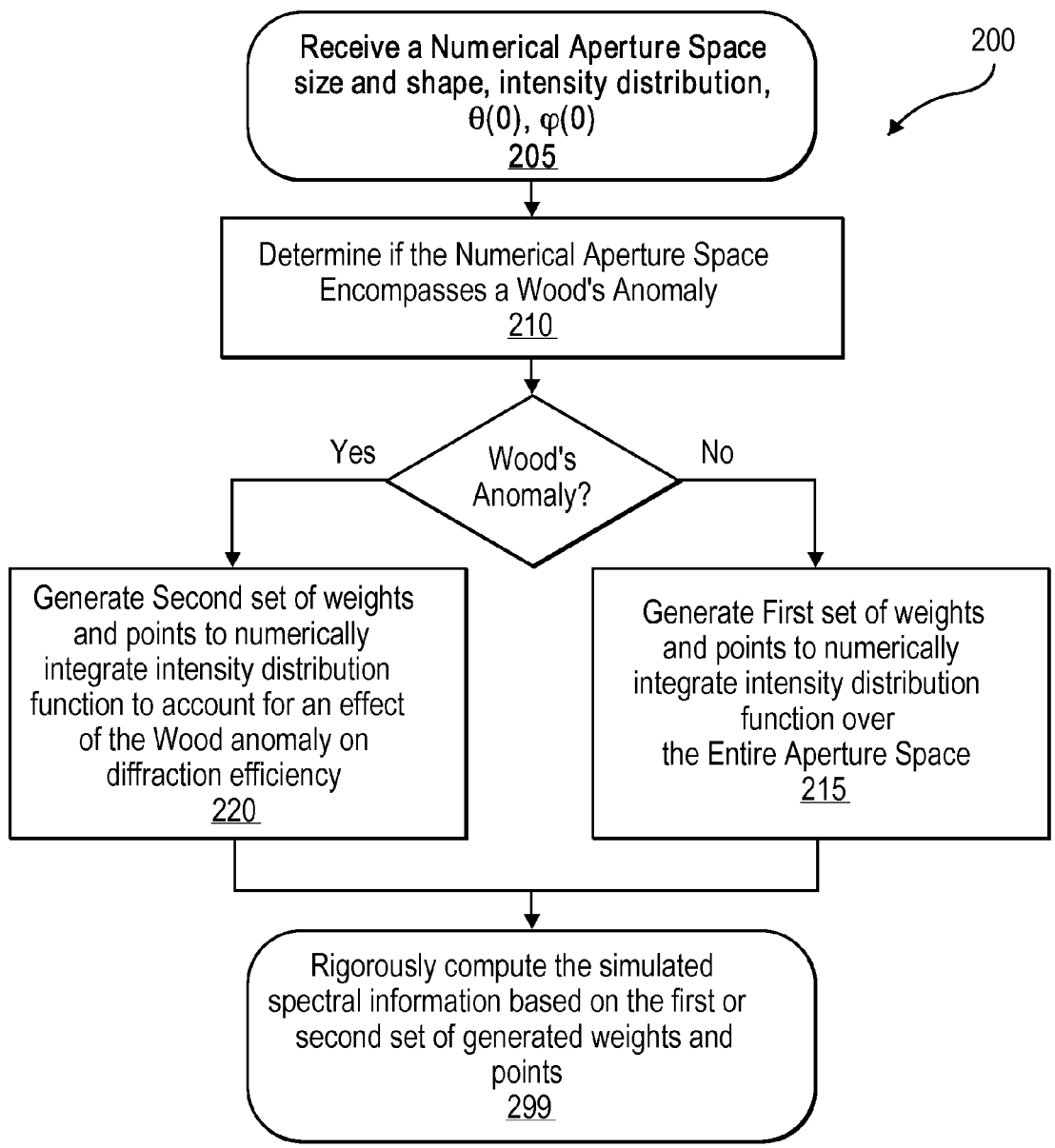
FIG. 2 is a flow diagram illustrating a method for integrating over a numerical aperture space based on a determination of the presence of a Wood anomaly, in accordance with an embodiment.
Figure 5:
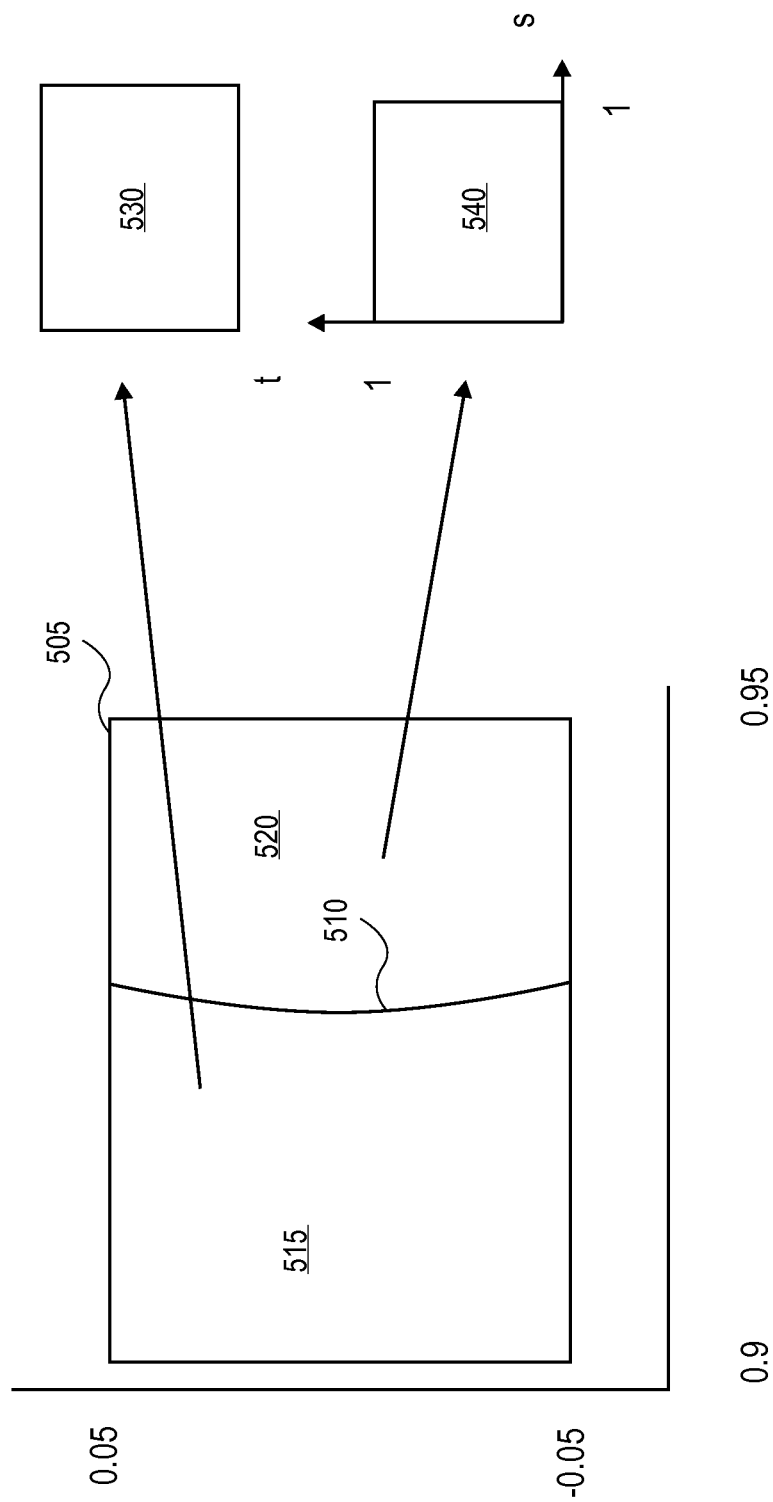
FIG. 5 illustrates a mapping of subregions of a numerical aperture space into unit squares for integration, in accordance with an embodiment of the present invention.

At operation 210, FIG. 2, a determination is made whether a Wood anomaly for a particular order m is located inside the numerical aperture space of the incident light. Generally, operation 210 entails computing curves that define the Wood anomaly based on the illumination and diffracting structure parameters received at operation 205. Such curves are portions of a Rayleigh circle that pass through the numerical aperture. FIG. 5 illustrates a Wood anomaly curve 510 passing through a rectangular numerical aperture 505. Positive and negative diffractive orders may be tested using the parameters received in operation 205.

In response to no Rayleigh singularity being determined to fall within the numerical aperture space, the method 200 proceeds to operation 215 where a first set of weights and nodes is generated to numerically integrate an intensity distribution function over the entire aperture space. For example, a standard Gaussian quadrature (cubature) routine is performed. If instead, a Wood anomaly is determined to lie within the numerical aperture space, the method 200 proceeds to operation 220 where a second set of weights and nodes are generated to account for the effect the anomaly has on diffraction efficiency.

At operation 299, simulated spectral information (e.g., spectral response of the target diffracting structure at a fixed angle of incidence) is then rigorously computed (e.g., by RCWA) at either the first or second set of points (nodes) and the respective weights applied to the evaluations.

Figure 3A:
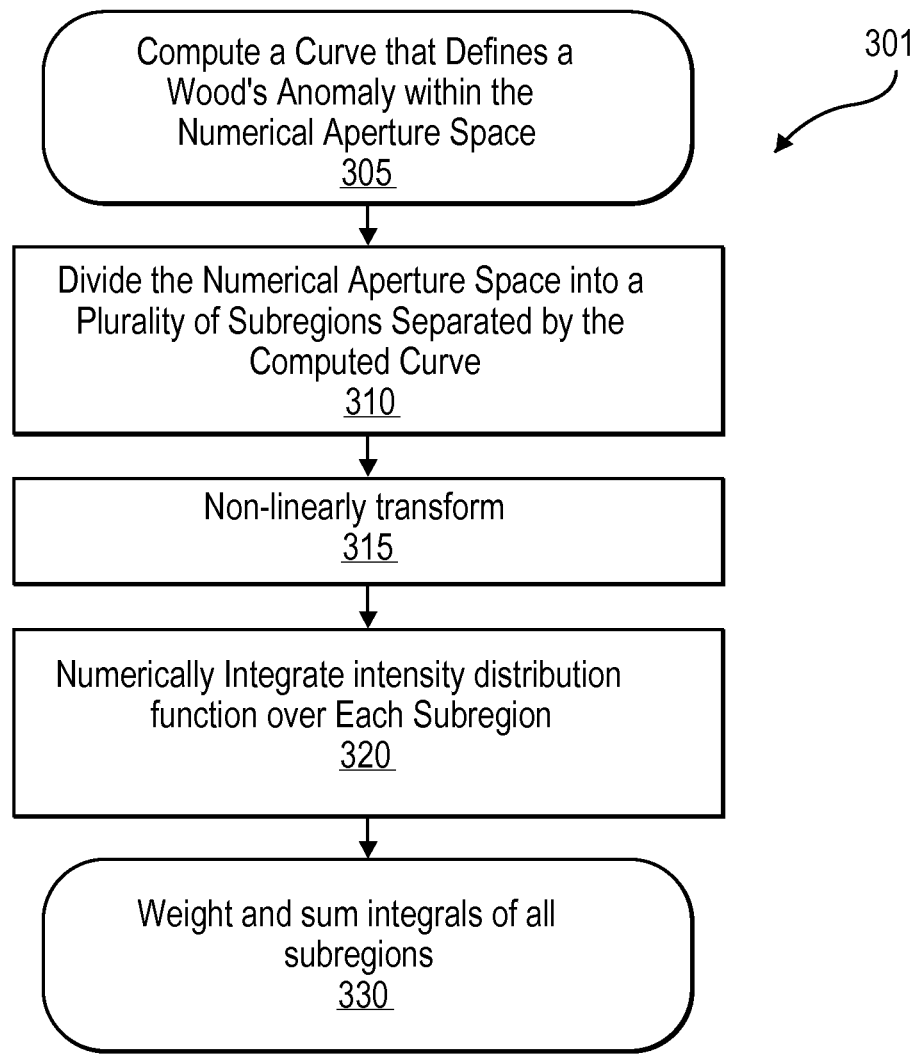
FIG. 3A is a flow diagram illustrating a first method for integrating over a numerical aperture space in which a Wood anomaly is found, in accordance with an embodiment.

FIG. 3A is a flow diagram illustrating in more detail a method 301 for integrating over a numerical aperture space in which a Wood anomaly is found, in accordance with an embodiment of method 200. Method 302 may therefore be performed as part of operation 220 in method 200. Although the description of the method 302 is succinct to avoid obscuring the embodiments of present invention, the interested reader will find relevant information in the publication, "*Effective Schema for the Rigorous Modeling of Grating Diffraction with Focused Beams*," Bischoff et al., Applied Optics, Vol. 50, No. 16, June 2011, the entirety of which is hereby incorporated by reference for all purposes.

Referring to FIG. 3A, an analytic expression for a curve defining a Wood anomaly with the numerical aperture space is determined at operation 305. The Wood anomaly condition is where the component of the wave vector in a normal direction is zero. The normal component of the wave vector may be derived for a given diffracting structure from a general dispersion equation. For a 1D grating, such as in FIG. 4A, the curve for the Wood anomaly reduces to $$1 - \left(\sin\theta\cos\phi + n\frac{\lambda}{p}\right)^2 - \sin^2\theta\sin^2\phi = 0 \qquad \text{(Eq. 1)}$$

Where n is the diffraction order. Similarly, for a 2D grating, such as in FIG. 4B, the curve for the Wood anomaly reduces to:

$$\vec{k}_0 = \sin\theta\cos\phi\hat{x} + \sin\theta\sin\phi\hat{y} \qquad \text{(Eq. 2)}$$

Where $\hat{x}$ and $\hat{y}$ are the unit vectors in the x and y-directions and $\vec{k}_0$ is the incident light which may be provided for diffraction order pairs (m, n), as:

$$\vec{k}_{m,n} = \vec{k}_0 + n\vec{k}\lambda + m\vec{Q}\lambda \qquad \text{(Eq. 3)}$$

where $\vec{K}$ and $\vec{Q}$ are reciprocal lattice vectors denoted as $\vec{a}$ and $\vec{b}$, describing the repeating cell of the 2D grating. The Wood anomaly condition is then:

$$1 - \|\vec{K_{n,m}}\|^2 = 0 \quad \text{(Eq. 4)}$$

The Wood anomaly curve(s) (e.g., Eq. 1 and 4) define a set of Rayleigh locations over a predetermined range of wavelength, azimuth angle ϕ, and incident angle θ for a parameter of the target diffracting structure (e.g., pitch p for a one dimensional grating or set of predetermined reciprocal lattice vectors $\vec{K}$ and $\vec{Q}$ for a two dimensional grating).

At operation 310, the numerical aperture space is divided into a plurality of subregions separated by the curve(s) computed at operation 310 and an outer boundary of the numerical aperture as defined by the aperture shape parameter. As such, intersections of the numerical aperture space and the Wood anomaly curve(s) are determined based on the shape of the numerical aperture. For a circularly shaped aperture ($NA^2 = x^2 + y^2$), the Rayleigh circles for the positive and negative orders occur pair-wise in the numerical aperture space with wavelength λ determining the locations of a Wood anomaly curve within the numerical aperture space. For the rectangular shaped aperture space 505 illustrated in FIG. 5, the Wood anomaly curve 510 corresponds to a minus second-order (m=−2).

Next, each of the subregions generated at operation 310 is then to be numerically integrated. In one embodiment, the subregions are first mapped to a unit square. FIG. 5 illustrates a mapping of subregions 515 and 520 of the numerical aperture space 505, as separated by the Wood anomaly curve 510, into the unit squares 530 and 540. Subregion 515 is bounded by the aperture rim on the left and Wood anomaly curve 510 on the right. Subregion 520 is bounded by the aperture rim on the right and Wood anomaly curve 510 on the left. Areas of the subregions sum to $2NA_y(NA_{max} - NA_{min})$, where $NA_y$ is the y-dimension aperture boundary for the chief ray ($θ_i = 0$) and $NA_{min,max} = \sin(θ_0 \pm \sin^{-1}(NA_x))$. The mapping operation generally entails converting the Wood anomaly curves (e.g., Eq. 1 and Eq. 4) into Cartesian coordinates (e.g., where x=sin θ cos ϕ and y=sin θ sin ϕ) and using new coordinates (s,t) to arrive at a the mapping:

$$y(s,t) = y_1 + (y_2 - y_1)t = NA_y(2t - 1) \quad \text{(Eq. 5)}$$

and $$x(s,t) = x_0 + s(x_1(y) - x_0) \quad \text{(Eq. 6)}$$

for the subregions 520 and 515, respectively. The mapped or transformed integral I may then be expressed as $$I = \int_0^1 \int_0^1 g(s,t) |J(s,t)| ds dt \quad \text{(Eq. 7)}$$

where |J(s,t)| is the determinant of the Jacobi matrix. Partial derivatives of each subregion (e.g., 515 and 520) may then be determined.

Because Gaussian quadrature is based on optimum polynomial interpolation, if the function (Eq. 7) is not of polynomial type such as square root of x, Gaussian quadrature can be very poorly suited for this type of integration. Therefore, in the exemplary embodiment, singular behavior of the Wood anomaly, (which is a square root singularity) is suppressed at operation 315 by applying a nonlinear transformation to the mapped integral (Eq. 7). For example a function with square root singularity at the origin can be eliminated by a transformation, such as $x = t^2$, so that:

$$\int_0^1 f(x^{1/2}) dx = 2 \int_0^1 f(t) t dt. \quad \text{(Eq. 8)}$$

With the transformation, the new integrand 2f(t)t is well behaved. A more general transformation can be written as:

$$x'(t) = \frac{(n+m+1)!}{n!m!} \tau^n (1-\tau)^m, \quad \text{(Eq. 9)}$$

$$x(t) = \frac{(n+m+1)!}{n!m!} \int_0^t \tau^n (1-\tau)^m d\tau.$$

Typically, one may choose n, m=0,1. With such a transformation, a one dimensional integral can be transformed in the following manner:

$$\int_0^1 f(x) dx = \int_0^1 f(x(t)) x'(t) dt \quad \text{(Eq. 10)}$$

$$= \frac{(n+m+1)!}{n!m!} \int_0^1 f(x(t)) t^n (1-t)^m dt$$

$$\approx \frac{(n+m+1)!}{n!m!} \sum_i f(x(t_i)) t_i^n (1-t_i)^m w_i$$

When f(x) is singular at either 0 or 1, or both, n,m is chosen so that x'(t)=0 for t at 0, or 1, or both. It has been determined through practice that this type of nonlinear transformation is highly advantageous as ensuring a faster speed of convergence. The transformation can be helpful even when Wood anomalies are outside but close to the apertures. In further embodiments where the diffracting structure has a higher dimension, a tensor product nonlinear transformation is employed (e.g. applied for 2D squares).

At operation 320, a numeric quadrature formula is then applied to integrate over the unit squares (e.g., 530, 540). For example, for a 1D diffracting structure, Gaussian quadrature may be performed for each subregion and for a 2D diffracting structure, Gaussian cubature may be performed for each subregion. The coordinate values of the quadrature (cubature) formula are inserted for all points (s,t). X, Y coordinates of these points are determined by inserting these values into Eqs. 5 and 6. The incidence angles θ and ϕ are calculated from the Cartesian coordinates x, y (e.g., x=sin θ cos ϕ and y=sin θ sin ϕ). The rigorous diffraction computation is run for these angles using standard techniques (e.g., RCWA) and the resulting spectral signal values are multiplied by the prefactor of the integral and the associated weight of the cubature formula and summed up to yield an approximate evaluation of the integral for each subregion (e.g., 515 and 520). As such, where a Wood anomaly is within the numerical aperture spacer, operation 299 (FIG. 2) entails performing operation 320 for each subregion and then performing operation 330, where the subregion integral evaluations, as weighted on basis of relative area $$\left( e.g., \text{ weight of subregion} = \frac{\text{area of subregion}}{\text{total area of aperture}} \right),$$

are summed.

Figure 6:
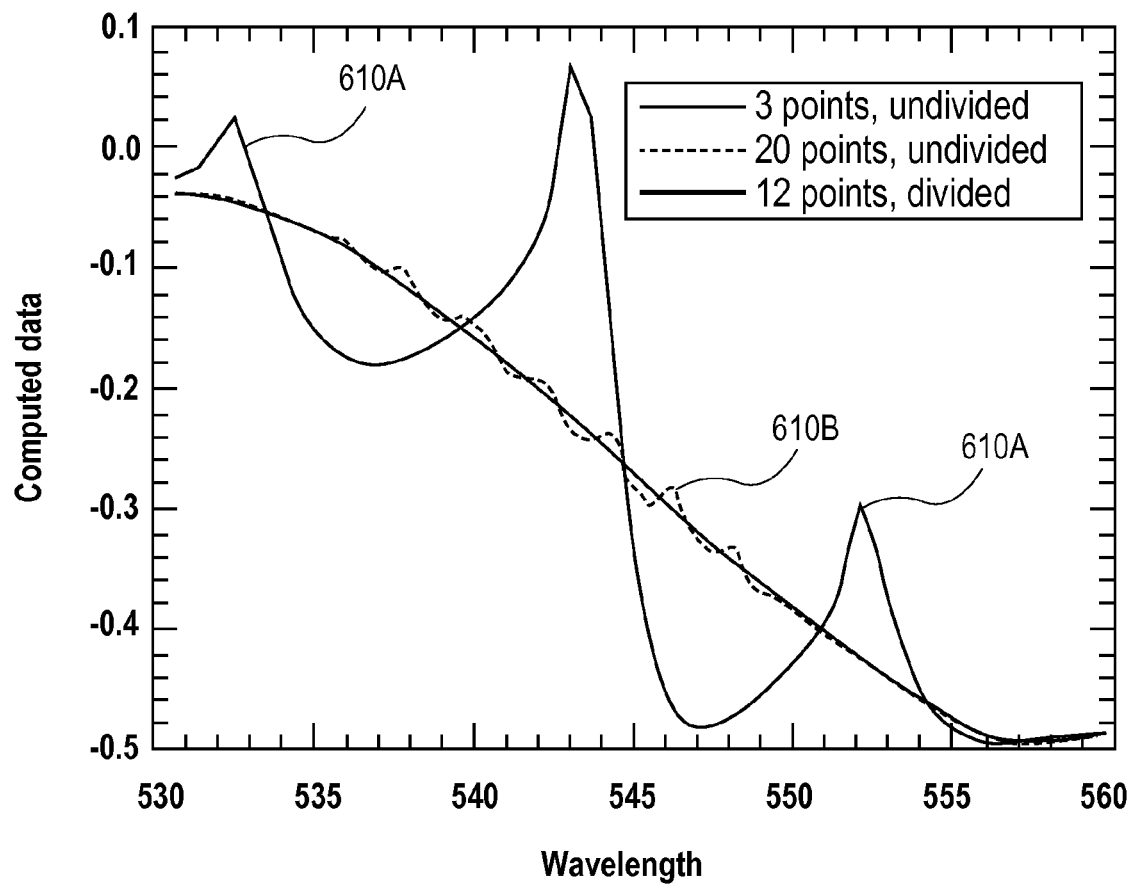
FIG. 6 illustrates computed spectral information determined for an embodiment of the method illustrated in FIG. 3A compared to spectral information determined with conventional integration techniques.

FIG. 6 illustrates simulated spectral information for an embodiment of the method 301 (FIG. 3A) compared to spectral information determined with a conventional integration technique which does not divide the numerical aperture based on Wood anomaly curves but rather treats the entire numerical aperture as a single domain. As shown, where fewer points (e.g., 3 points) are utilized, the simulated spectral information includes discontinuity peaks 610A which correspond to Rayleigh singularities. Such peaks do not exist in a measured spectrum (e.g., generated by detector 110 of FIG. 1). These discontinuity peaks remain even when many more points (nodes) are utilized in conventional techniques (e.g., peaks 610B for the simulated signal for a 20 point quadrature). Note however the greater smoothness of the curve labeled "divided," where the simulated spectral information is generated corresponding to the method 301 with numerical aperture division into subregions based on Wood anomaly curves and a subsequent nonlinear transformation. Even though only 12 quadrature points are utilized, the smoother curve is much better matched to experimentally measured intensity distributions.

Figure 3B:
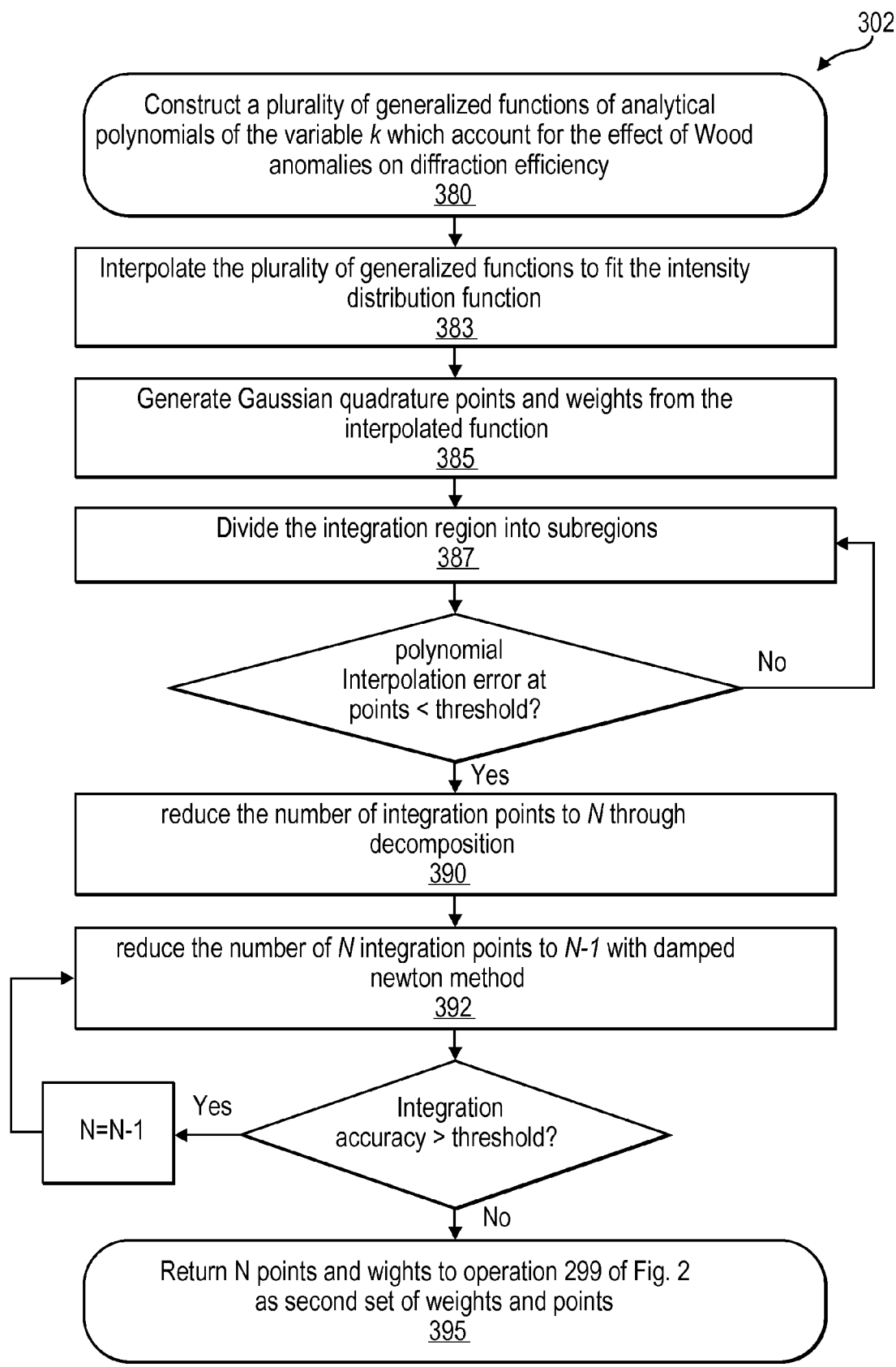
FIG. 3B is a flow diagram illustrating a second method for integrating over a numerical aperture space in which a Wood anomaly is found, in accordance with an embodiment.

FIG. 3B is a flow diagram illustrating a method 302 for integrating over a numerical aperture space in which a Wood anomaly is found, in accordance with another embodiment of the method 200. For example, method 302 may be performed as part of operation 220 in method 200. In method 302, generalized Gaussian quadrature is utilized and the interested reader is referred to the publication, "*A Nonlinear Optimization Procedure for Generalized Gaussian Quadratures*", Bremer et al., SIAM J. Sci. Comput., 32, pp. 1761-1788 (2010) for a detailed description of known techniques for determining points and weights for approximation of an integral for one dimensional integrals. For embodiments of the present invention, the function to be integrated is assumed to have the form:

$$f(\vec{k}) = g_0(\vec{k}) + \sum_{n,m} g_{n,m}(\vec{k})\sqrt{|1-|\vec{k}_{n,m}|^2|} \qquad (Eq.\ 11)$$

This generalized function includes the square root-type Wood anomaly condition, for example as arrived at for the Eq. 4, and is therefore a generalized function that accounts for the effect of the Wood anomaly on diffraction efficiency. At operation 380, a plurality of such generalized functions are constructed where the indices n, m are chosen so that $\vec{k}_{n,m}$ is within the integration zone (i.e., numerical aperture space) and the functions $g(\vec{k})$ are analytic polynomials of the variable k. The g functions are well behaved functions free of singularities. The summation is over m and n so that the Wood anomaly curves are within the integration region or fairly close to the region. For a rectangular type of aperture, a tensor-product of Legendre polynomials may be used for 2D NA integrations, namely for each function $g_{n,m}(\vec{k})$, scale the variables $k_x$ and $k_y$ so that in each subregion they can be expressed in terms of the following basis functions:

$$g^{(i,j)}(\vec{k}) = L_i(q_x)L_j(q_y) \qquad (Eq.\ 12)$$

where $q_x$ and $q_y$ are scaled so that they are both in [−1,1]. For embodiments with non-rectangular regions, a transformation into squares is performed.

At operation 383, the plurality of generalized functions is interpolated to fit the intensity distribution function described above in Eqs. 11 and 12 (e.g., received at operation 205 in FIG. 2). At operation 385, Gaussian quadrature (cubature) points (nodes) and weights are generated based on the known behavior of the generalized functions as the integrand. In the exemplary embodiment, the numerical aperture is adaptively divided into smaller subregions at operation 387 until the polynomial interpolation at Gaussian quadrature (cubature) points in each subregion achieves a threshold level of accuracy. For example, assume a given rectangle region and a set of functions $\phi_m(x, y)$, m=1, 2, . . . , M, are to be interpolated over the region with preset points. First we set the number of points in the given region to be 2K×2K, 2K in each direction. These points are determined from the Gaussian quadrature and are denoted as $x_i$, $y_j$, j=1, 2, . . . , 2K. For each function $\phi_m(x, y)$, m=1, 2, . . . , M, we construct its tensor-product polynomial approximation as:

$$\phi_m(x,y) \approx \sum_{i,j=0}^{2K-1} \alpha_m^{(i,j)} L_i(x) L_j(y) \qquad (Eq.\ 13)$$

Error is then computed as $$\varepsilon^2 = \sum_{i+j=K}^{2K-1} |\alpha_m^{(i,j)}|^2.$$

If ε is larger than the prescribed accuracy (e.g., $10^{-4}$) for any m value, the region is divided into 4 rectangles and operation 387 repeated. In other embodiments, a region is divided into 2 rectangles, the direction of which can be determined by comparing the values of $$\varepsilon_x^2 = \sum_{i=K,j=0}^{2K-1} |\alpha_m^{(i,j)}|^2 \text{ and } \varepsilon_y^2 = \sum_{i=0,j=K}^{2K-1} |\alpha_m^{(i,j)}|^2.$$

If the former is greater than the latter, the region is divided in the x-direction, otherwise it is divided in the y-direction. Where the desired accuracy is achieved, K×K points composed of tensor-product K point Gaussian quadrature points are used. All the tensor-product Gaussian quadrature points at the lowest level are collected and the points at their parent levels are discarded.

For the sake of simplicity, the tensor-product quadrature points may be condensed in to one single notation:

$$\vec{r}_i = (x_i, y_j), W_i = w_i w_j A \qquad (Eq.\ 14)$$

where A is the area of the subregion and w's are the 1D Gaussian quadrature weights. The orthogonal functions $u_m(\vec{r}_i) = u_{im}/\sqrt{W_i}$ are then obtained by performing a singular value decomposition (SVD) on matrix A, where $A_{im} = \phi_m(\vec{r}_i)$ as A=UΣV*. In such a decomposition, assuming that A is an N×M matrix, and N>M, then $U^T U = V V^T = I$, where I is an M×M identity matrix, and Σ is a diagonal matrix whose elements are greater or equal to zero and ordered in such a way that the first element is the largest. Truncating the elements that are small to zero entails a good approximation of the original matrix.

At operation 390, the Gaussian quadrature (cubature) determined for the sub regions as an accurate integration scheme. QR decomposition is employed with column pivoting to reduce the number of integration points obtained from operation 385 based on prescribed integration accuracy. First we construct a matrix B through $$\sum_i \phi_m(\vec{r}_i) W_i = \sum_i \phi_m(\vec{r}_i) W_i^{1/2} W_i^{1/2} \quad \text{(Eq. 15)}$$
$$\equiv \sum_i B_{m,i} W_i^{1/2}$$
$$= I_m,$$
$$B_{m,i} \equiv \phi_m(\vec{r}_i) W_i^{1/2}$$

Next, a pivoted QR factorization of matrix B is performed so that $$B = Q \begin{pmatrix} R_{1,1} & R_{1,2} \\ 0 & R_{2,2} \end{pmatrix} P \rightarrow Q \begin{pmatrix} R_{1,1} & R_{1,2} \\ 0 & R_{2,2} \end{pmatrix} PW^{1/2} \quad \text{(Eq. 16)}$$
$$= I \rightarrow \begin{pmatrix} R_{1,1} & R_{1,2} \\ 0 & R_{2,2} \end{pmatrix} PW^{1/2}$$
$$= Q^T I$$

where Q is an orthogonal matrix and P is a pivoting matrix which simply exchanges the indices of $\vec{r}_i$'s. The factorization process is stopped when $|R_{2,2}|$ is small. The points associated with matrix $R_{2,2}$ are dropped and only those associated with matrix $R_{1,1}$ are retained. A new set of weights whose components are $\tilde{W}_i = z_i W_i^{1/2}$ are determined after finding the associated solutions to $R_{1,1} z = Q^T I$.

At operation 392, integration points N may then be reduced incrementally using, for example, damped Newton method to solve the following nonlinear optimization problem:

$$\min \sum_{i=1}^{N-1} \left| \sum_{j=1}^{N-1} \tilde{W}_j u_i(\tilde{r}_j) - \int u_i(\vec{r}) d\vec{r} \right|^2, \quad \text{(Eq. 17)}$$

from N points to N−1 points where $u_i$ is the tensor-product of Lagrange polynomials. Note that with each increment, the point with the least contribution to the integral is removed. This process repeats until further reduction leads to an error larger than the prescribed accuracy. The integration points and weights, as generated at operation 385, or as reduced at operations 390, 392, accounting for the effect of the Wood anomaly and are then employed in operation 299, to rigorously compute the simulated spectral information.

Figure 7:
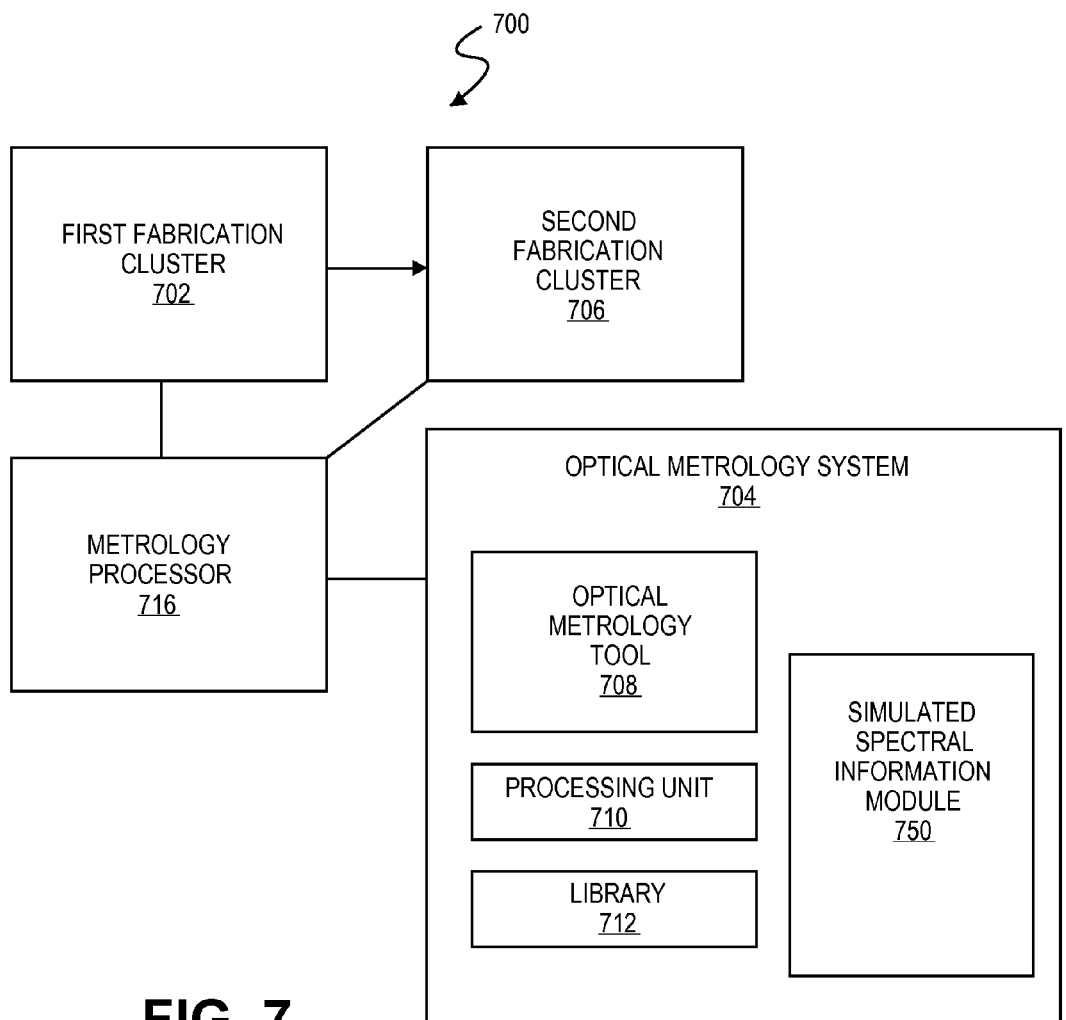
FIG. 7 is a block diagram of a system to implement the methods illustrated in FIGS. 3A and 3B for determining and utilizing profile parameters for automated process and equipment control, in accordance with an embodiment.

FIG. 7 is a block diagram of a system 700 to implement one or more of the methods illustrated in FIGS. 2, 3A and 3B for determining and utilizing profile parameters for automated process and equipment control, in accordance with an embodiment. System 700 includes a first fabrication cluster 702 and optical metrology system 704. System 700 also includes a second fabrication cluster 706. Although the second fabrication cluster 706 is depicted in FIG. 7 as being subsequent to first fabrication cluster 702, it should be recognized that second fabrication cluster 706 can be located prior to first fabrication cluster 702 in system 700 (e.g. and in the manufacturing process flow). A photolithographic process, such as exposing and/or developing a photoresist layer applied to a wafer, can be performed using first fabrication cluster 702. In one exemplary embodiment, optical metrology system 704 includes an optical metrology tool 708 and processing unit 710. Optical metrology tool 708 is configured to measure a diffraction signal off of a target diffracting structure. If the measured diffraction signal and the simulated diffraction signal match, one or more values of the profile parameters are presumed equal the one or more values of the profile parameters associated with the simulated diffraction signal.

In one exemplary embodiment, optical metrology system 704 also includes a library 712 with a plurality of simulated (i.e. calculated) diffraction signals and a plurality of values of one or more profile parameters associated with the plurality of simulated diffraction signals. Each of the plurality of simulated diffraction signals may be generated by the methods described herein to account for an effect of Wood anomaly on a diffraction efficiency following one or more of the methods illustrated herein (e.g., FIGS. 2, 3A and 3B).

Metrology processing unit 710 can compare a measured diffraction signal generated for a target diffracting structure by the optical metrology tool 708 to the plurality of simulated diffraction signals in the library. When a matching simulated diffraction signal is found, the one or more values of the profile parameters associated with the matching simulated diffraction signal in the library is assumed to be the one or more values of the profile parameters characterizing the measured structure.

System 700 also includes a metrology processor 716. In one exemplary embodiment, processing unit 710 can transmit the one or more values of the one or more profile parameters to metrology processor 716. Metrology processor 716 can then adjust one or more process parameters or equipment settings of first fabrication cluster 702 based on the one or more values of the one or more profile parameters determined using optical metrology system 704. Metrology processor 716 can also adjust one or more process parameters or equipment settings of the second fabrication cluster 706 based on the one or more values of the one or more profile parameters determined using optical metrology system 704. As noted above, fabrication cluster 706 can process the wafer before or after fabrication cluster 702.

Figure 8:
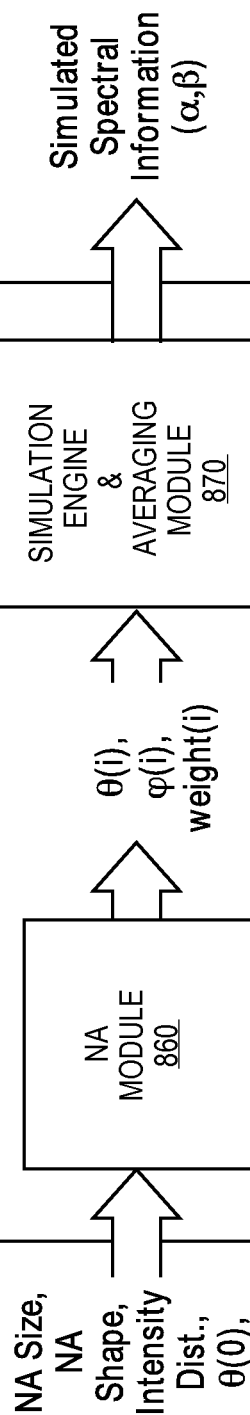
FIG. 8 is a process flow diagram illustrating input and output data streams of data processing modules employed in the system illustrated in FIG. 7.

System 700 includes a simulated spectral information module 750 that includes in FIG. 8 an NA module 860 and a simulation engine and averaging module 870. The simulated spectral information module 750 may be implemented in either hardware (e.g., ASIC, FPGA, etc.) or software (e.g., as an instance executed by the processing unit 710). The simulated spectral information module 750 is to generate the spectral information for the simulated diffraction signals stored in the library 712.

FIG. 8 is a schematic diagram illustrating input and output data streams and data processing modules employed in the simulated spectral information module 750 illustrated in FIG. 7. Depending on implementation, the data processing module may be implemented in hardware (e.g., ASIC or FPGA) or software (e.g., instantiated by the processing unit 710). In particular embodiment, the NA module 860 is to perform determinations of whether a particular set of parameters specifying a numerical aperture for the optical metrology tool 708 (e.g., NA shape, NA size), and/or specifying an illumination wavelength, and/or specifying a target diffracting structure to be illuminated by the optical metrology tool 708 will be affected by a Wood anomaly. The NA module 860 then outputs a data stream comprising a set of weights(i) and points(i) determined based on whether a Wood anomaly is within the numerical aperture, for approximation of an intensity distribution function integral over the numerical aperture. The simulation engine and averaging module 870 is to receive the output data stream from the NA module 860 and perform numerical aperture averaging (integration) as described elsewhere herein (e.g., by performing RCWA at the set of points (i) and averaging each point(i) with the weight(i)). The simulated spectral information module 750 then outputs the simulated spectral information (e.g., for storage in library 712).

Figure 9:
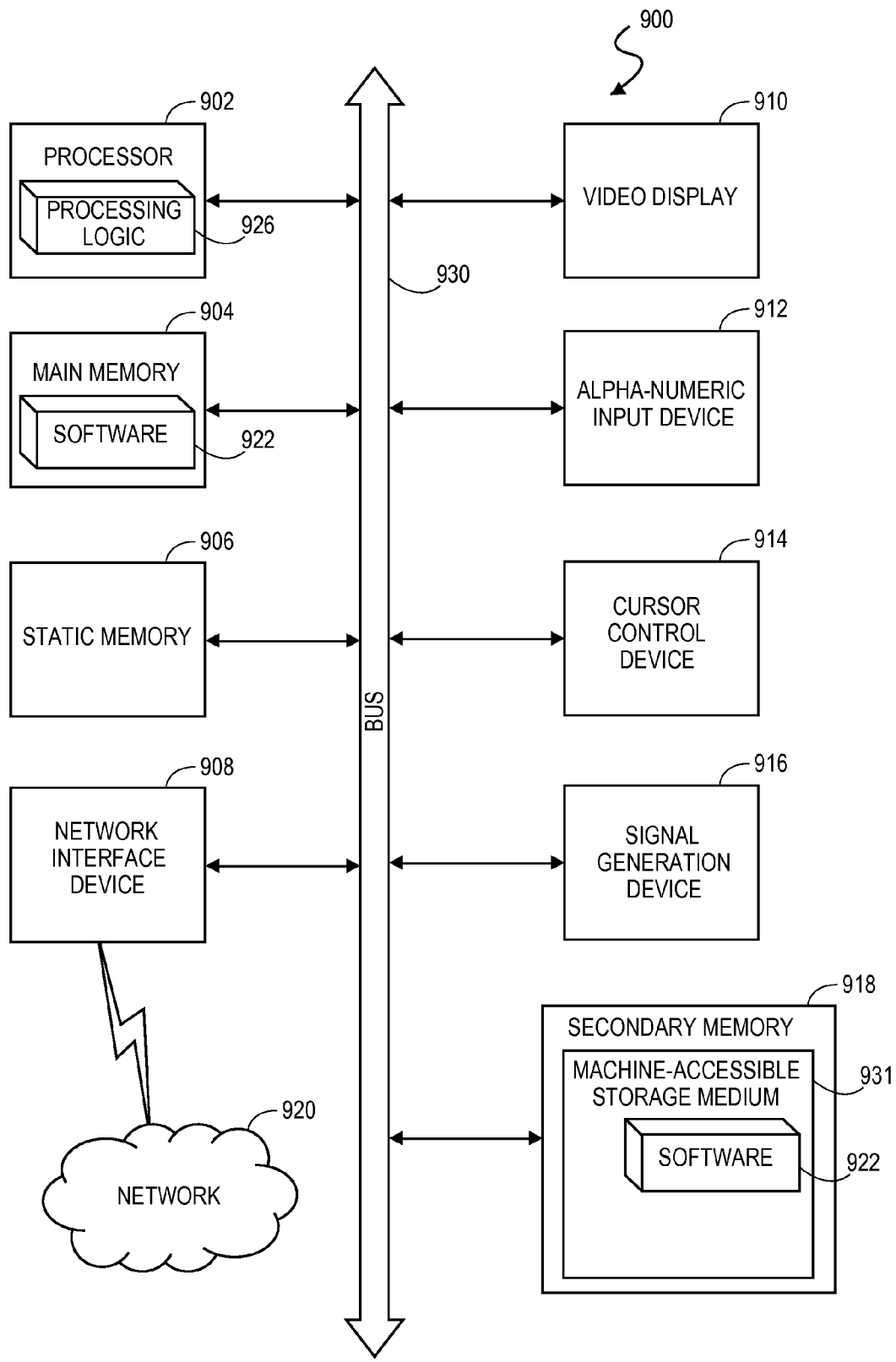
FIG. 9 is a block diagram of a processing system to perform one or more of the functional blocks illustrated in FIGS. 7 and 8, in accordance with an embodiment.

FIG. 9 is a block diagram of a computer system 900 to implement the methods illustrated in FIGS. 2, 3A and 3B, by executing set of instructions, for example as the processing unit 710 (FIG. 7). The computer system 900 may operate in the capacity of a server or a client machine in a client-server network environment, or as a peer machine in a peer-to-peer (or distributed) network environment. The computer system 900 may be a personal computer (PC) or any known computing platform capable of executing a set of instructions (sequential or otherwise) that specify actions to be taken by that computer platform. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 900 includes a processor 902, a main memory 904 (e.g., read-only memory (ROM), flash memory, dynamic random access memory (DRAM) such as synchronous DRAM (SDRAM) or Rambus DRAM (RDRAM), etc.), a static memory 906 (e.g., flash memory, static random access memory (SRAM), etc.), and a secondary memory 918 (e.g., a data storage device), which communicate with each other via a bus 930.

Processor 902 represents one or more general-purpose processing devices such as a microprocessor, central processing unit, or the like. More particularly, the processor 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 902 may also be one or more special-purpose processing devices such as an application specific integrated circuit (ASIC), a field programmable gate array (FPGA), a digital signal processor (DSP), network processor, or the like. Processor 902 is configured to execute the processing logic 926 for automatically performing the operations discussed herein.

The computer system 900 may further include a network interface device 908. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 916 (e.g., a speaker).

The secondary memory 918 may include a machine-accessible storage medium (or more specifically a computer-readable storage medium) 931 on which is stored one or more sets of instructions (e.g., software 922) embodying any one or more of the methodologies or functions described herein. The software 1722 may also reside, completely or at least partially, within the main memory 904 and/or within the processor 902 during execution thereof by the computer system 900, the main memory 904 and the processor 902 also constituting machine-readable storage media. The software 922 may further be transmitted or received over a network 920 via the network interface device 908.

While the machine-accessible storage medium 931 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, optical and magnetic media, and other known non-transitory storage media.

In accordance with an embodiment of the present invention, a machine-accessible storage medium has instructions stored thereon which cause a data processing system to perform a method of simulating spectral information for structural analysis using OCD metrology. The method includes determining if there is a Wood anomaly within the numerical aperture space, numerically integrating over the numerical aperture space by generating a first set of points and weights, in response to determining there is no Wood anomaly or, in response to determining there is a Wood anomaly, by generating a second set of points and weights that account for an effect of the Wood anomaly on diffraction efficiency, and rigorously computing the simulated spectral information based on the first or second set of generated points and weights.

Figure 10A:
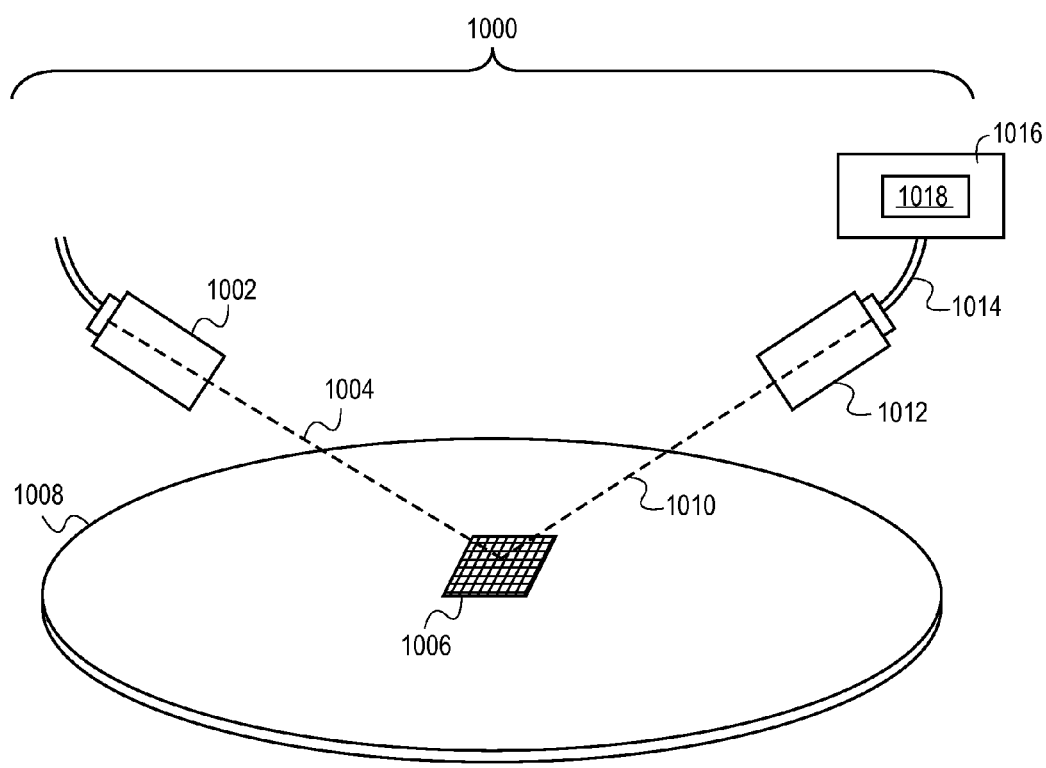
FIG. 10A is a schematic illustrating the utilization of OCD metrology to determine parameters of structures on a semiconductor wafer, in accordance with embodiments of the present invention.

FIG. 10A is a schematic illustrating the utilization of OCD metrology to determine parameters of structures on a semiconductor wafer, in accordance with embodiments of the present invention. An optical metrology system 1000 (which may be utilized as the optical metrology tool 708 in FIG. 7) includes a metrology beam source 1002 projecting a metrology beam 1004 at the target diffracting structure 1006 of a wafer 1008. The metrology beam 1004 is projected at the incidence angle θ towards the target structure 1006. The ellipsometer may, in one embodiment, use an incidence angle of approximately 60° to 70°, or may use a lower angle (possibly close to 0° or near-normal incidence) or an angle greater than 70° (grazing incidence). The diffraction beam 1010 is measured by a metrology beam receiver (detector) 1012. The diffraction beam data 1014 is transmitted to a profile application server 1016. The profile application server 1016 may compare the measured diffraction beam data 1014 against a library 1018 of simulated diffraction beam data representing varying combinations of critical dimensions of the target structure and resolution.

In one exemplary embodiment, the library 1018 instance best matching the measured diffraction beam data 1014 is selected. It is to be understood that although a library of diffraction spectra or signals and associated hypothetical profiles is frequently used to illustrate concepts and principles, the present invention applies equally to a data space including simulated diffraction signals and associated sets of profile parameters, such as in regression, neural network, and similar methods used for profile extraction. The hypothetical profile and associated critical dimensions of the selected library 1016 instance is assumed to correspond to the actual cross-sectional profile and critical dimensions of the features of the target structure 1006. The optical metrology system 1000 may utilize a reflectometer, an ellipsometer, or other optical metrology device to measure the diffraction beam or signal.

In order to facilitate the description of embodiments of the present invention, an ellipsometric optical metrology system is used to illustrate the above concepts and principles. It is to be understood that the same concepts and principles apply equally to the other optical metrology systems, such as reflectometric systems. In an embodiment, the optical scatterometry is a technique such as, but not limited to, optical spectroscopic ellipsometry (SE), beam-profile reflectometry (BPR), beam-profile ellipsometry (BPE), and ultra-violet reflectometry (UVR). In a similar manner, a semiconductor wafer may be utilized to illustrate an application of the concept. Again, the methods and processes apply equally to other work pieces that have repeating structures.

Figure 10B:
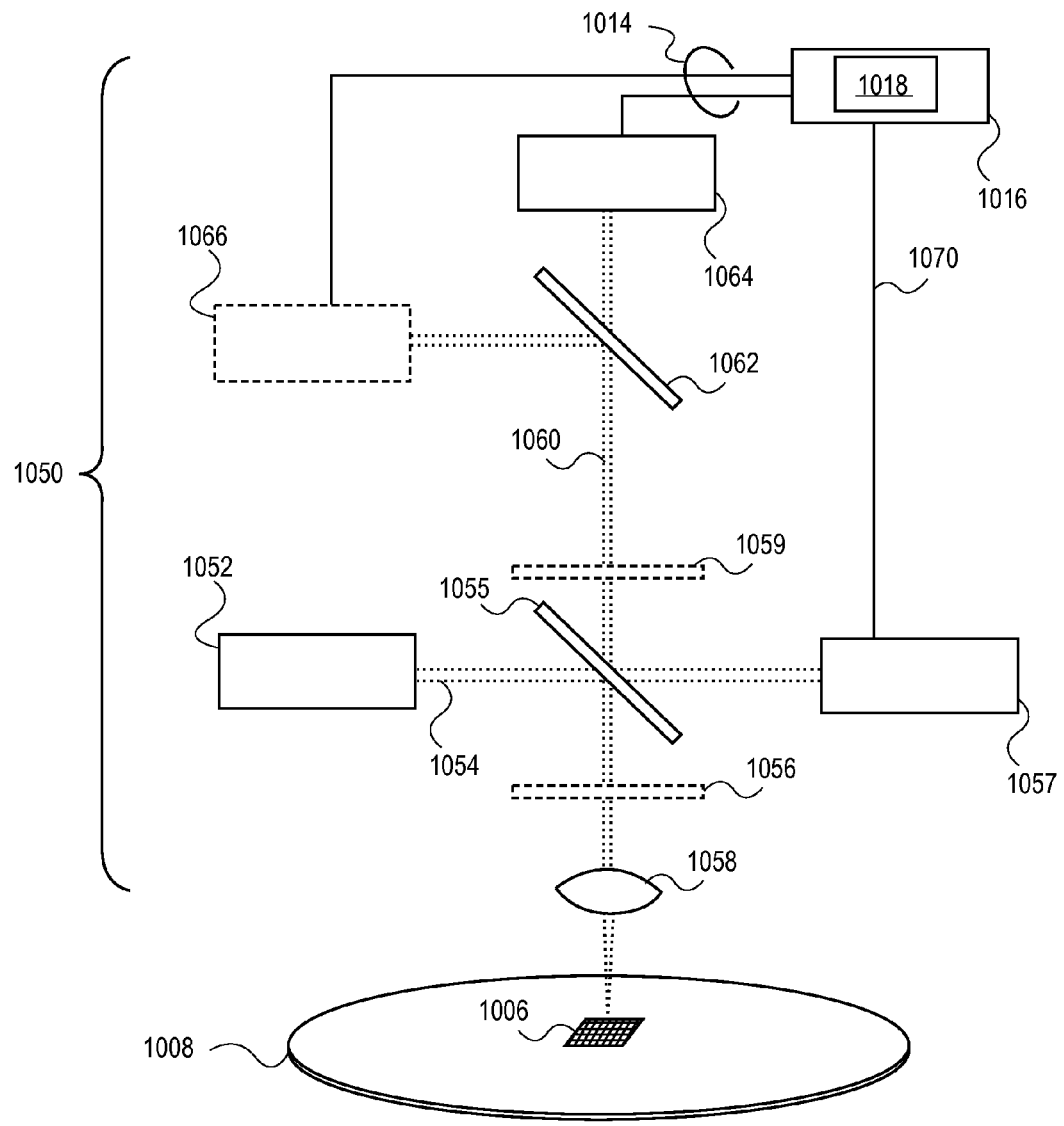
FIG. 10B is a schematic diagram illustrating the utilization of beam-profile reflectometry and/or beam-profile ellipsometry to determine parameters of structures on a semiconductor wafer, in accordance with embodiments of the present invention.

FIG. 10B is a schematic illustrating the utilization of OCD metrology to determine parameters of structures on a semiconductor wafer, in accordance with embodiments of the present invention. The optical metrology system 1050 (which may be utilized as the optical metrology tool 708 in FIG. 7) includes a metrology beam source 1052 generating a polarized metrology beam 1054. Preferably this metrology beam has a narrow bandwidth of 10 nm or less. In some embodiments, the source 1052 is capable of outputting beams of different wavelengths by switching filters or by switching between different lasers or super-bright light emitting diodes. Part of this beam is reflected from the beam splitter 1055 and focused onto the target structure 1606 of a wafer 1008 by objective lens 1058, which has a high numerical aperture (NA), preferably an NA of approximately 0.9 or 0.95. The part of the beam 1054 that is not reflected from the beam splitter is directed to beam intensity monitor 1057. The metrology beam may, optionally, pass through a quarter-wave plate 1056 before the objective lens 1058. After reflection from the target the reflected beam 1060 passes back through the objective lens and is directed to one or more detectors. If optional quarter-wave plate 1056 is present, the beam will pass back through that quarter-wave plate before being transmitted through the beam splitter 1055. After the beam-splitter, the reflected beam 1060 may optionally pass through a quarter-wave plate at location 1059 as an alternative to location 1056. If the quarter-wave plate is present at location 1056, it will modify both the incident and reflected beams. If it is present at location 1059, it will modify only the reflected beam. In some embodiments, no wave plate may be present at either location, or the wave plate may be switched in and out depending on the measurement to be made. It is to be understood that in some embodiments it might be desirable that the wave plate have a retardance substantially different from a quarter wave, i.e. the retardance value might be substantially greater than, or substantially less than, 90°. A polarizer or polarizing beam splitter 1062 directs one polarization state of the reflected beam 1060 to detector 1064, and, optionally, directs a different polarization state to an optional second detector 1066. The detectors 1064 and 1066 might be one-dimensional (line) or two-dimensional (array) detectors. Each element of a detector corresponds to a different combination of AOI and azimuthal angles for the corresponding ray reflected from the target. The diffraction beam data 1014 from the detector(s) is transmitted to the profile application server 1016 along with beam intensity data 1070. The profile application server 1016 may compare the measured diffraction beam data 1014 after normalization or correction by the beam intensity data 1070 against a library 1018 of simulated diffraction beam data representing varying combinations of critical dimensions of the target structure and resolution.

For more detailed descriptions of systems that could measure the diffraction beam data or signals for use with the present invention, see U.S. Pat. No. 6,734,967, entitled FOCUSED BEAM SPECTROSCOPIC ELLIPSOMETRY METHOD AND SYSTEM, filed on Feb. 11, 1999, and U.S. Pat. No. 6,278,519 entitled APPARATUS FOR ANALYZING MULTI-LAYER THIN FILM STACKS ON SEMICONDUCTORS, filed Jan. 29, 1998, both of which are incorporated herein by reference in their entirety. These two patents describe metrology systems that may be configured with multiple measurement subsystems, including one or more of a spectroscopic ellipsometer, a single-wavelength ellipsometer, a broadband reflectometer, a DUV reflectometer, a beam-profile reflectometer, and a beam-profile ellipsometer. These measurement subsystems may be used individually, or in combination, to measure the reflected or diffracted beam from films and patterned structures. The signals collected in these measurements may be analyzed to determine parameters of structures on a semiconductor wafer in accordance with embodiments of the present invention.

It is to be understood that the above description is illustrative, and not restrictive. For example, while flow diagrams in the figures show a particular order of operations performed by certain embodiments of the invention, it should be understood that such order may not be required (e.g., alternative embodiments may perform the operations in a different order, combine certain operations, overlap certain operations, etc.). Furthermore, many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. The scope of the invention should, therefore, be determined with reference to the appended claims, along with the full scope of equivalents to which such claims are entitled.

What is claimed is:

1. A computer implemented method for generating simulated spectral information in optical critical dimension (OCD) metrology, the method comprising:
   receiving an intensity distribution function over a numerical aperture space for a target diffracting structure;
   generating a set of points and weights for a non-linear transformation of the intensity distribution function over a plurality of subregions within the numerical aperture space; and
   rigorously computing the simulated spectral information based on the set of generated points and weights.

2. The method of claim 1, further comprising performing the non-linear transformation by squaring the intensity distribution function in each subregion.

3. The method of claim 1, further comprising determining if there is a Wood anomaly within the numerical aperture space by determining if the Rayleigh condition for the target diffracting structure is satisfied for any wavelength, azimuth angle, and incident angle within a predetermined range.

4. The method of claim 3, wherein the generating a set of points and weights for a non-linear transformation of the intensity distribution function is in response to determining there is a Wood anomaly; and wherein the method further comprises generating a second set of points and weights, in response to determining there is no Wood anomaly wherein the second set of points and weights is generated over the entire aperture space without first dividing the aperture space into the plurality of subregions.

5. The method of claim 1, wherein generating the set of points and weights for the non-linear transformation further comprises:
   computing a curve that defines a Wood anomaly within the numerical aperture space;
   dividing the numerical aperture space into a plurality of subregions separated by the computed curve; and
   generating points and weights for each of the subregions.

6. The method of claim 5, wherein computing the curve that defines a Wood anomaly further comprises:
   solving for a set of Rayleigh locations over a predetermined range of wavelength, azimuth angle, and incident angle for a parameter of the target diffracting structure, wherein the parameter is a predetermined pitch for a one dimensional grating or is a set of predetermined lattice vectors corresponding to unit cells for a two dimensional grating.

7. The method of claim 5, wherein generating points and weights for each of the subregions further comprises:
mapping each of the subregions to a separate unit square; and
performing a numerical quadrature of the transformed intensity distribution function over each separate unit square.

8. The method of claim 7, further comprising determining a weighted sum of subregion integrals approximated by the numerical quadrature, wherein the weighting is based on relative areas of the numerical aperture space corresponding to each subregion.

9. The method of claim 7, wherein performing the numerical quadrature further comprises:
performing Gaussian quadrature integration for a one dimensional numerical aperture; and
performing Gaussian cubature integration for a two dimensional numerical aperture.

10. A non-transitory computer readable media comprising instructions stored thereon, which when executed by a processing system cause the processor to perform the method of claim 1.

11. A computer implemented method for generating simulated spectral information in optical critical dimension (OCD) metrology, the method comprising:
receiving an intensity distribution function over a numerical aperture space for a target diffracting structure;
generating points and weights for an interpolated function fitted to the intensity distribution function; and
rigorously computing the simulated spectral information based on the set of generated points and weights.

12. The method of claim 11, wherein generating the points and weights for the interpolated function fitted to the intensity distribution function further comprises:
constructing a plurality of generalized functions of analytical polynomials;
interpolating the plurality of generalized functions to fit the intensity distribution function; and
generating the points and weights from a function of the interpolation.

13. The method of claim 12, wherein the plurality of generalized functions include a term accounting for an effect of Wood anomalies on diffraction efficiency.

14. The method of claim 12, wherein generating the points and weights from the function of the interpolation comprises adaptively dividing the integration region into subregions until polynomial interpolation at Gaussian quadrature points in each subdomain reaches a predetermined accuracy threshold; and
generating at least one Gaussian quadrature integration point for each of the subregions.

15. The method of claim 14, further comprising performing a QR decomposition, where $Q^T Q=I$ and R is an upper triangular matrix whose elements below the diagonal are all zero, to eliminate at least one of the integration points based on a predetermined integration accuracy threshold.

16. The method of claim 14, further comprising iteratively performing a damped Newton method to reduce the number of integration points one at a time until a further reduction in the number of integration points is unable to reach the predetermined integration accuracy threshold.

17. A non-transitory computer readable media comprising instructions stored thereon, which when executed by a processing system cause the processor to perform the method of claim 11.

18. An optical critical dimension (OCD) measurement apparatus, comprising:
a light source;
a detector to collect measured spectral information from the light source as diffracted by a target grating disposed on a substrate being measured by the apparatus;
a simulated spectral information module to generate simulated spectral information by numerically integrating a non-linear transformed intensity distribution function by Gaussian quadrature using a set of weights and points that account for the effect of Wood anomalies on diffraction efficiency; and
logic to compare the measured spectral information and the simulated spectral information and generate an estimate of a critical dimension of a feature in the target grating.

19. The OCD measurement apparatus of claim 18, wherein the simulated spectral information module is further to divide a numerical aperture space into subregions along a curve defining a Wood anomaly.

20. The OCD measurement apparatus of claim 18, wherein the simulated spectral information module is to:
compute the curve that defines a Wood anomaly within the numerical aperture space; and
generate points and weights for each subregion.

21. The OCD measurement apparatus of claim 18, wherein the simulated spectral information module is to perform the non-linear transformation of the intensity distribution function in each subregion.

* * * * *